US007597661B2

(12) United States Patent
Long (10) Patent No.: US 7,597,661 B2
(45) Date of Patent: Oct. 6, 2009

(54) MEDICAL INSTRUMENT HAVING A CATHETER AND METHOD FOR USING A CATHETER

(75) Inventor: Gary L. Long, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 523 days.

(21) Appl. No.: 11/432,674

(22) Filed: May 11, 2006

(65) Prior Publication Data

US 2007/0282187 A1    Dec. 6, 2007

(51) Int. Cl.
*A61B 1/00* (2006.01)
(52) U.S. Cl. .................. 600/115; 600/372; 600/373; 600/114; 600/118; 606/41
(58) Field of Classification Search .......... 600/101, 600/114–118, 120, 145, 146, 152, 372–374, 600/377, 380–382, 393; 607/115, 116, 133, 607/138, 147, 148; 606/32, 34, 41
See application file for complete search history.

(56) References Cited

U.S. PATENT DOCUMENTS

| 3,470,876 A | 10/1969 | Barchilon |
| 3,521,620 A | 7/1970 | Cook |
| 3,791,387 A | 2/1974 | Itoh |
| 3,799,151 A | 3/1974 | Fakaumi et al. |
| 3,805,791 A | 4/1974 | Seuberth et al. |
| 4,326,530 A | 4/1982 | Fleury, Jr. |
| 4,493,320 A | 1/1985 | Treat |
| 4,638,802 A | 1/1987 | Okada |
| 4,890,602 A | 1/1990 | Hake |

(Continued)

FOREIGN PATENT DOCUMENTS

DE    19729499    1/1999

(Continued)

OTHER PUBLICATIONS

Ginsberg, G.G., "Colonoscopy with the variable stiffness colonoscope," Gastrointestinal Endoscopy, vol. 58, No. 4 (2003).

(Continued)

*Primary Examiner*—John P Leubecker
*Assistant Examiner*—Samuel Candler
(74) *Attorney, Agent, or Firm*—Gerry Gressel (57) ABSTRACT

A medical instrument includes a catheter having a distal end insertable within a body lumen and having longitudinally spaced apart and circumferentially-protruding first and second pods. The first pod has a first exterior surface with a first surface portion. The first surface portion includes an energizable first electrode pair of circumferentially-spaced-apart electrodes. The first surface portion has a shape adapted to advance the first pod within the lumen upon contraction of muscular lumen tissue contacting an energized first electrode pair. The second pod has a second exterior surface with a second surface portion. The second surface portion includes an energizable second electrode pair of circumferentially-spaced-apart electrodes. The second surface portion has a shape adapted to advance the second pod within the lumen upon contraction of muscular lumen tissue contacting an energized second electrode pair. A method for using a medical catheter is described wherein each pod includes an inflatable balloon.

20 Claims, 7 Drawing Sheets

U.S. PATENT DOCUMENTS

| | | | |
|---|---|---|---|
| 4,963,147 | A | 10/1990 | Agee et al. |
| 5,035,696 | A | 7/1991 | Rydell |
| 5,201,732 | A | 4/1993 | Parins et al. |
| 5,201,741 | A | 4/1993 | Dulebohn |
| 5,250,060 | A | 10/1993 | Carbo et al. |
| 5,342,299 | A | 8/1994 | Snoke et al. |
| 5,346,504 | A | 9/1994 | Ortiz et al. |
| 5,353,807 | A | 10/1994 | DeMarco |
| 5,397,304 | A | 3/1995 | Truckai |
| 5,409,453 | A | 4/1995 | Lundquist et al. |
| 5,431,671 | A | 7/1995 | Nallakrishnan |
| 5,433,721 | A | 7/1995 | Hooven et al. |
| 5,441,499 | A | 8/1995 | Fritzsch |
| 5,531,664 | A | 7/1996 | Adachi et al. |
| 5,531,686 | A | 7/1996 | Lundquist et al. |
| 5,618,294 | A | 4/1997 | Aust et al. |
| 5,706,827 | A | 1/1998 | Ehr et al. |
| 5,776,080 | A | 7/1998 | Thome et al. |
| 5,792,165 | A | 8/1998 | Kileman et al. |
| 5,810,807 | A | 9/1998 | Ganz et al. |
| 5,836,947 | A | 11/1998 | Fleischman |
| 5,848,986 | A | 12/1998 | Lundquist et al. |
| 5,897,554 | A | 4/1999 | Chia et al. |
| 5,972,012 | A | 10/1999 | Ream et al. |
| 6,066,102 | A | 5/2000 | Townsend et al. |
| 6,074,408 | A | 6/2000 | Freeman |
| 6,152,918 | A | 11/2000 | Padilla et al. |
| 6,203,494 | B1 | 3/2001 | Moriyama |
| 6,352,503 | B1 | 3/2002 | Matsui et al. |
| 6,371,907 | B1 | 4/2002 | Hasegawa et al. |
| 6,423,059 | B1 | 7/2002 | Hanson et al. |
| 6,443,943 | B1 | 9/2002 | Ouchi |
| 6,443,944 | B1 | 9/2002 | Doshi et al. |
| 6,450,948 | B1 | 9/2002 | Matsuura et al. |
| 6,451,014 | B1 | 9/2002 | Wakikaido et al. |
| 6,454,703 | B1 | 9/2002 | Ide |
| 6,454,758 | B1 | 9/2002 | Thompson |
| 6,475,222 | B1 | 11/2002 | Berg et al. |
| 6,482,149 | B1 | 11/2002 | Torii |
| 6,488,658 | B1 * | 12/2002 | Long ........................... 604/113 |
| 6,500,189 | B1 | 12/2002 | Lang et al. |
| 6,569,105 | B1 | 5/2003 | Kortenbach et al. |
| 6,579,300 | B2 | 6/2003 | Griego et al. |
| 6,602,267 | B2 | 8/2003 | Castaneda |
| 6,612,992 | B1 | 9/2003 | Hossack et al. |
| 6,709,388 | B1 * | 3/2004 | Mosse et al. ................. 600/114 |
| 6,730,097 | B2 | 5/2004 | Dennis |
| 6,743,240 | B2 | 6/2004 | Smith et al. |
| 6,764,441 | B2 * | 7/2004 | Chiel et al. .................. 600/115 |
| 6,866,626 | B2 * | 3/2005 | Long et al. ................... 600/114 |
| 7,060,024 | B2 | 6/2006 | Long et al. |
| 7,060,025 | B2 | 6/2006 | Long et al. |
| 7,118,587 | B2 | 10/2006 | Dycus et al. |
| 2001/0037084 | A1 | 11/2001 | Nardeo |
| 2002/0017515 | A1 | 2/2002 | Obata et al. |
| 2002/0095168 | A1 | 7/2002 | Griego et al. |
| 2002/0177802 | A1 | 11/2002 | Moutafis et al. |
| 2003/0074014 | A1 | 4/2003 | Castaneda |
| 2003/0125788 | A1 * | 7/2003 | Long ........................... 607/133 |
| 2003/0153866 | A1 * | 8/2003 | Long et al. .................... 604/28 |
| 2003/0181785 | A1 | 9/2003 | Viebach et al. |
| 2003/0195492 | A1 | 10/2003 | Gobron et al. |
| 2003/0208219 | A1 | 11/2003 | Aznoian et al. |
| 2004/0034343 | A1 | 2/2004 | Gillespie et al. |
| 2004/0044350 | A1 | 3/2004 | Martin et al. |
| 2004/0068291 | A1 | 4/2004 | Suzuki |
| 2004/0092953 | A1 | 5/2004 | Salameh et al. |
| 2004/0097919 | A1 | 5/2004 | Wellman et al. |
| 2004/0143159 | A1 | 7/2004 | Wendlandt |
| 2004/0193016 | A1 | 9/2004 | Root et al. |
| 2004/0230096 | A1 | 11/2004 | Stefanchik et al. |
| 2005/0183733 | A1 * | 8/2005 | Kawano et al. ............. 128/899 |
| 2005/0222587 | A1 | 10/2005 | Jinno et al. |
| 2005/0234296 | A1 | 10/2005 | Saadat et al. |
| 2005/0272975 | A1 | 12/2005 | McWeeney et al. |
| 2005/0273084 | A1 | 12/2005 | Hinman et al. |
| 2005/0273085 | A1 | 12/2005 | Hinman et al. |
| 2006/0009711 | A1 | 1/2006 | Gingrich et al. |

FOREIGN PATENT DOCUMENTS

| | | |
|---|---|---|
| EP | 0027704 | 4/1981 |
| EP | 0397489 | 11/1990 |
| EP | 1849421 | 10/2007 |
| JP | 2004-154164 | 6/2004 |
| WO | WO 96/00030 | 1/1996 |
| WO | WO 97/12557 | 4/1997 |
| WO | 97/35135 | 9/1997 |
| WO | 01/08737 | 2/2001 |
| WO | 01/93938 | 12/2001 |
| WO | 02/43797 | 6/2002 |
| WO | 03/053225 | 7/2003 |
| WO | 2005/113051 | 12/2005 |
| WO | 2006/019291 | 2/2006 |
| WO | 2006/122279 | 11/2006 |

OTHER PUBLICATIONS

Brooker, J.C. et al., "A new variable stiffness colonoscope makes colonoscopy easier: a randomised controlled trial," Gut 2000, 46, pp. 801-805 (2000).

Rex, D.K., "Effect of Variable Stiffness Colonoscopes on Cecal Intubation Times for Routine Colonoscopy by an Experienced Examiner in Sedated Patients," Endoscopy; 33 (1), pp. 60-64 (2001).

Shah, S.G., et al., "Magnetic imaging of colonoscopy: an audit of looping, accuracy and ancillary maneuvers," Gastrointestinal Endoscopy, vol. 52, No. 1, pp. 1-8 (2000).

Shah, S.G., et al., "The variable stiffness colonoscope: assessment of efficacy by magnetic endoscope imaging," Gastrointestinal Endoscopy, vol. 56, No. 2, pp. 195-201 (2002).

"Sensors-Resistance," Smart Engineering Group (1999).

Examination Report, European Application No. 07251728.7 (Dec. 17, 2008).

* cited by examiner

MEDICAL INSTRUMENT HAVING A CATHETER AND METHOD FOR USING A CATHETER

FIELD OF THE INVENTION

The present invention is related generally to medical equipment, and more particularly to a medical instrument having a medical catheter and to a method for using a medical catheter.

BACKGROUND OF THE INVENTION

Examples of known catheters include, without limitation, flexible insertion tubes of endoscopes (including flexible insertion tubes of colonoscopes and enteroscopes). The insertion tube has an articulatable distal end portion controlled by wires running from the distal end portion to control knobs on the handle of the endoscope. A wide angle video camera in the distal end of the insertion tube permits medical observation. Medical devices, such as a medical needle-knife or a medical snare, are part of an endoscopic system and are insertable into the working channel(s) of the insertion tube of the endoscope and are translatable to extend from the distal end portion for medical treatment. In use, the distal end of the insertion tube is inserted into a body lumen of a patient. The user manually pushes on a proximal tube portion to advance the distal end of the insertion tube within the body lumen for medical observation and/or medical treatment. In a serpentine body lumen, such as the colon, the articulatable distal end of the insertion tube can become misaligned in the body lumen and become blocked by lumen tissue from further advancement. Then, if the user further pushes on the proximal tube portion, the insertion tube forms undesirable loops which the user must correct before realigning the distal end of the insertion tube and further advancing the insertion tube within the body lumen. U.S. Pat. No. 6,866,626 discloses performing a colonoscopy using a self-propelled capsule connected to the distal end of an umbilicus, wherein electrodes on the capsule stimulate muscular colon tissue to contract thereby advancing the capsule within the colon.

Still, scientists and engineers continue to seek improved medical instruments having a catheter and improved methods for using a catheter.

SUMMARY OF THE INVENTION

A first expression of an embodiment of the invention is for a medical instrument including a medical catheter. The medical catheter has a distal end, a centerline, a circumferentially-protruding first pod, and a circumferentially-protruding second pod. The distal end is insertable within a body lumen of a patient having muscular lumen tissue surrounding the body lumen. The centerline defines a longitudinal axis when the medical catheter is in an unflexed state. The first pod has a first exterior surface with a first surface portion. The first surface portion includes an energizable first electrode pair of circumferentially-spaced-apart electrodes. The first surface portion has a shape adapted to advance the first pod within the body lumen upon contraction of muscular lumen tissue contacting an energized first electrode pair. The second pod has a second exterior surface with a second surface portion. The second surface portion includes an energizable second electrode pair of circumferentially-spaced-apart electrodes. The second surface portion has a shape adapted to advance the second pod within the body lumen upon contraction of muscular lumen tissue contacting an energized second electrode pair. The second pod is proximally longitudinally spaced apart from the first pod.

A first expression of an alternate embodiment of the invention is for a medical instrument including a medical catheter and a controller. The medical catheter is a sheath and is adapted for installation over a flexible endoscope insertion tube. The installed medical catheter includes a distal end, a centerline, a circumferentially-protruding first pod, and a circumferentially-protruding second pod. The distal end is insertable within a body lumen of a patient having muscular lumen tissue surrounding the body lumen. The centerline defines a longitudinal axis when the installed medical catheter is in an unflexed state. The first pod has a first exterior surface with a first surface portion. The first surface portion includes an energizable first electrode pair of circumferentially-spaced-apart electrodes. The first surface portion has a shape adapted to advance the first pod within the body lumen upon contraction of muscular lumen tissue contacting an energized first electrode pair. The second pod has a second exterior surface with a second surface portion. The second surface portion includes an energizable second pair of circumferentially-spaced-apart electrodes. The second surface portion has a shape adapted to advance the second pod within the body lumen upon contraction of muscular lumen tissue contacting an energized second electrode pair. The second pod is proximally longitudinally spaced apart from the first pod. The controller is adapted to energize the first electrode pair for contraction of muscular lumen tissue contacting the first electrode pair and is adapted to energize the second electrode pair for contraction of muscular lumen tissue contacting the second electrode pair.

A method of the invention is for using a medical catheter. The medical catheter includes a distal end, a centerline, a circumferentially-protruding first pod, and a circumferentially-protruding second pod. The distal end is insertable within a body lumen of a patient having muscular lumen tissue surrounding the body lumen. The centerline defines a longitudinal axis when the medical catheter is in an unflexed state. The first pod has a first exterior surface with a first surface portion. The first surface portion includes an energizable first electrode pair of circumferentially-spaced-apart electrodes. The first surface portion has a shape adapted to advance the first pod within the body lumen upon contraction of muscular lumen tissue contacting an energized first electrode pair. The first pod includes an inflatable first balloon, wherein the first exterior surface is an inflated exterior surface of the first balloon. The second pod has a second exterior surface with a second surface portion. The second surface portion includes an energizable second pair of circumferentially-spaced-apart electrodes. The second surface portion has a shape adapted to advance the second pod within the body lumen upon contraction of muscular lumen tissue contacting an energized second electrode pair. The second pod is proximally longitudinally spaced apart from the first pod. The second pod includes an inflatable second balloon, wherein the second exterior surface is an inflated exterior surface of the second balloon. The method includes inserting the distal end within the body lumen. The method also includes manually advancing the medical catheter within the body lumen a first distance with the first and second balloons deflated and with the first and second electrode pairs not energized. The method also includes inflating the first and second balloons. The method also includes energizing the first electrode pair after the first balloon has been inflated. The method also includes energizing the second electrode pair after the second balloon has been inflated.

Several benefits and advantages are obtained from one or more of the expressions of several embodiments and the method of the invention. In one example, the pods are disposed proximate the distal end so that the self-advancing medical catheter will not form undesirable loops, as can be appreciated by those skilled in the art. In the same or a different example, each pod includes an inflatable balloon which supports the electrodes, which is deflated (resulting in a smaller catheter transverse cross-sectional size within the body lumen) when manual advancement of the medical catheter within the body lumen is desired, and which is inflated only when self-advancement of the medical catheter within the body lumen is desired. In the same or a different example, a controller simultaneously or sequentially energizes the first and second electrode pairs for more rapid advancement within the body lumen than is possible from a single electrode pair, wherein the electrode pairs are longitudinally spaced apart a distance ensuring that muscular lumen tissue contracted by one electrode pair will have enough time to relax before the self-advancing next electrode pair reaches the same muscular lumen tissue. In the same or a different example, the medical catheter is a sheath installed over an existing endoscope insertion tube improving the performance of existing endoscopes.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described expressions, embodiments, examples, etc. can be combined with any one or more of the other following-described expressions, embodiments, examples, etc.

Referring now to the Figures, wherein like numerals represent like elements throughout, FIGS. 1-5 illustrate an embodiment of the invention. A first expression of the embodiment of FIGS. 1-5 is for a medical instrument 10 including a medical catheter 12. The medical catheter 12 has a distal end 14, a centerline 16, a circumferentially-protruding first pod 18, and a circumferentially-protruding second pod 20. The distal end 20 is insertable within a body lumen 22 of a patient having muscular lumen tissue 24 surrounding the body lumen 22. The centerline 16 defines a longitudinal axis when the medical catheter 12 is in an unflexed state. The first pod 18 has a first exterior surface 26 with a first surface portion 28. The first surface portion 28 includes an energizable first electrode pair 30 of circumferentially-spaced-apart electrodes 32 and 34. The first surface portion 28 has a shape adapted to advance the first pod 18 (and hence the medical catheter 12) within the body lumen 22 upon contraction of muscular lumen tissue 24 contacting an energized first electrode pair 30. The second pod 20 has a second exterior surface 36 with a second surface portion 38. The second surface portion 38 includes an energizable second electrode pair 40 of circumferentially-spaced-apart electrodes 42 and 44. The second surface portion 38 has a shape adapted to advance the second pod 20 (and hence the medical catheter 12) within the body lumen 22 upon contraction of muscular lumen tissue 24 contacting an energized second electrode pair 40. The second pod 20 is proximally longitudinally spaced apart from the first pod 18.

Figure 1:
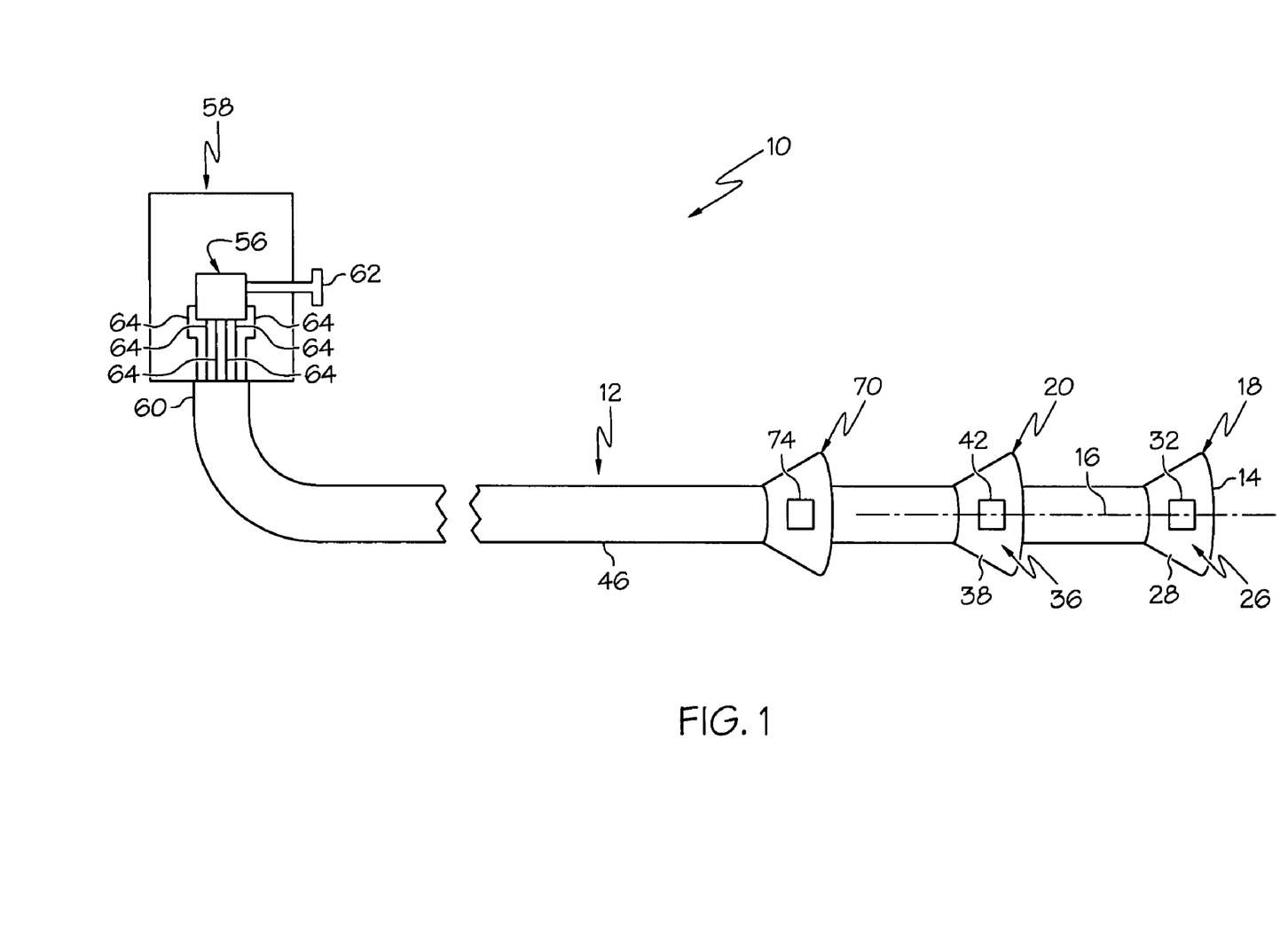
FIG. 1 is a schematic view of an embodiment of a medical instrument including a medical catheter and a controller, wherein the controller is located in a handpiece which is shown in cut-away.
Figure 2:
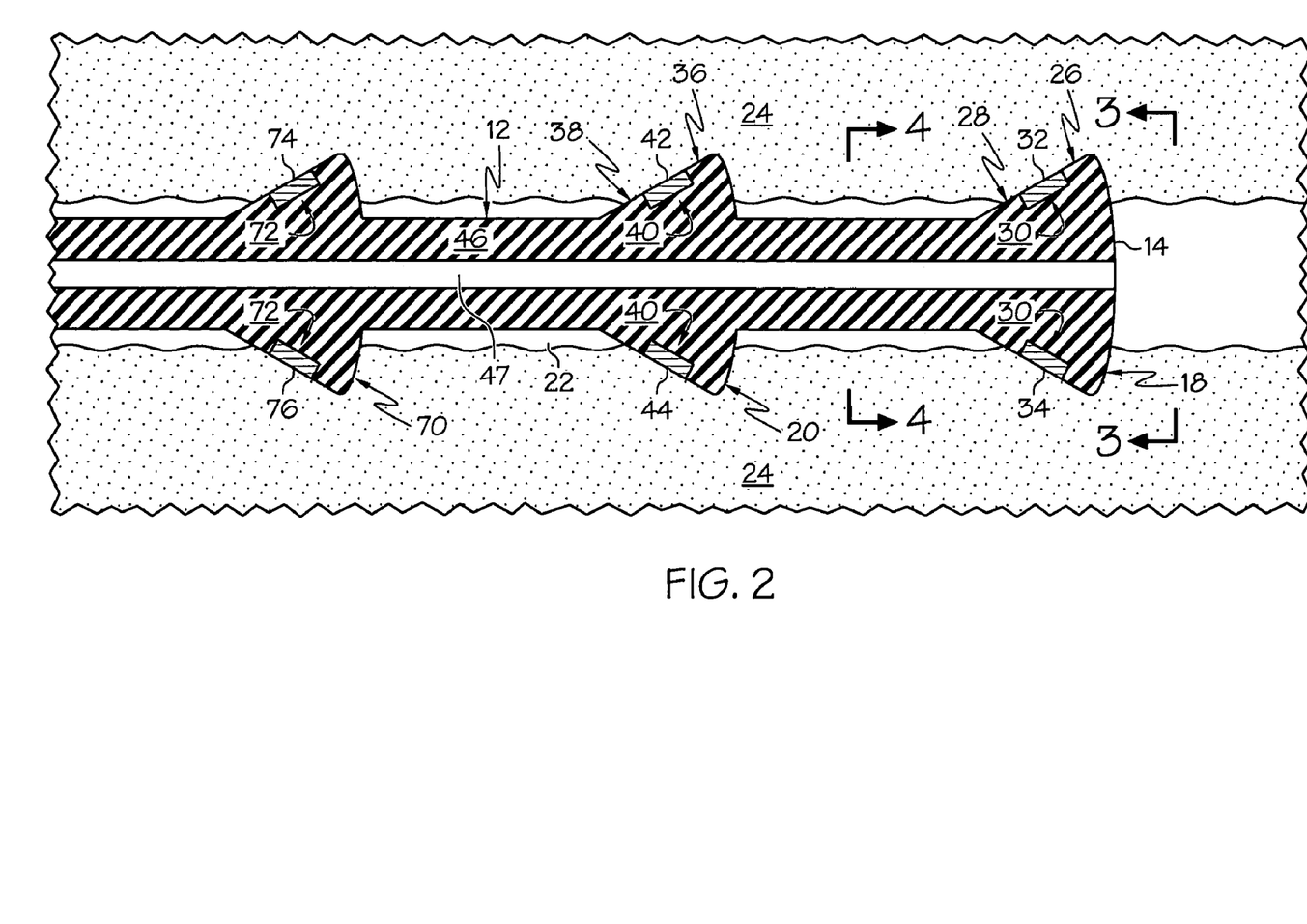
FIG. 2 is a cross sectional view of the distal portion of the medical catheter of FIG. 1 inserted within a body lumen of a patient, wherein the medical catheter of FIG. 2 has been rotated ninety degrees from the orientation shown in FIG. 1.
Figure 3:
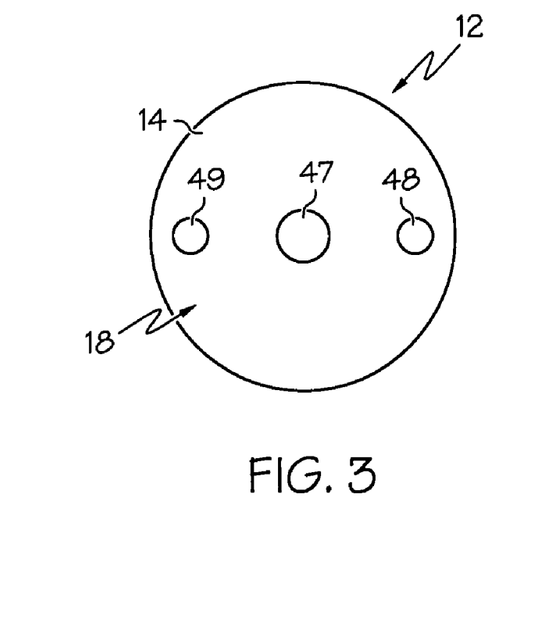
FIG. 3 is a view of the medical catheter of FIG. 2 taken along lines 3-3 of FIG. 2.
Figure 4:
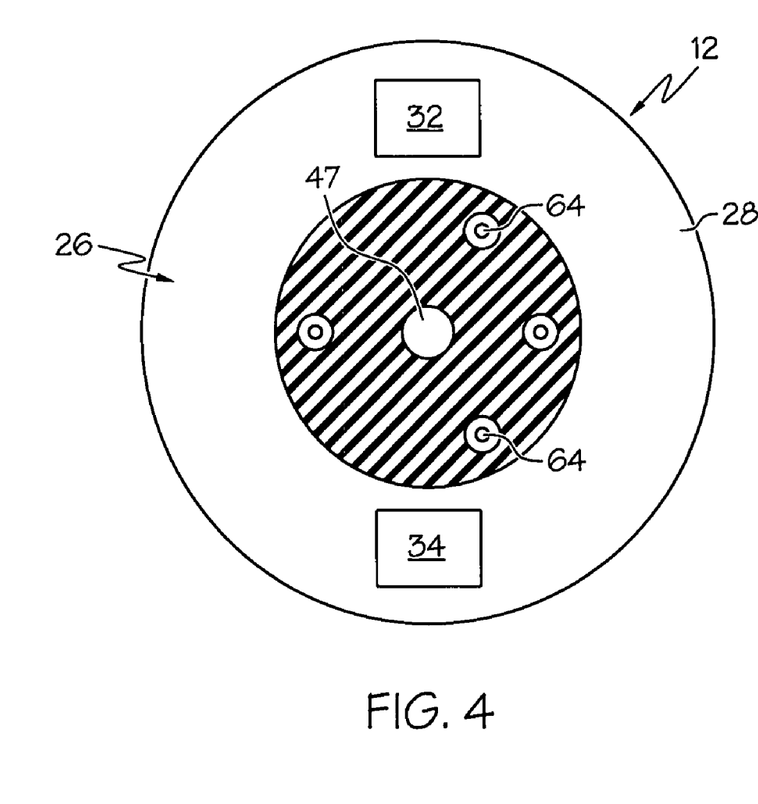
FIG. 4 is a cross sectional view of the medical catheter of FIG. 2 taken along lines 4-4 of FIG. 2.

In one deployment of the first expression of the embodiment of FIGS. 1-5, the first pod 18 is disposed proximate the distal end 14. In one variation, the first pod 18 is disposed at the distal end 14. In one variation, the first and second pods 18 and 20 are fully-circumferential protrusions. In one modification, each of the first and second surface portions 28 and 38 is an angled surface (such as a surface having a proximally-tapering conical shape as shown in FIG. 2), wherein contracting muscular lumen tissue 24 applies a force to the angled surface which advances the medical catheter 12 within the body lumen 22, as can be appreciated by the artisan. Other surface shapes are left to those skilled in the art. In one illustration, the first and second surface portions 28 and 38 each have at least one additional electrode pair (not shown).

In a first implementation of the first expression of the embodiment of FIGS. 1-5, the medical catheter 12 is a flexible endoscope insertion tube 46 having a working channel 47. In one variation, the endoscope insertion tube 46 includes a visualization device 48 disposed at the distal end 14. In one modification, the endoscope insertion tube 46 includes an illumination device 49 disposed at the distal end 114.

Figure 6:
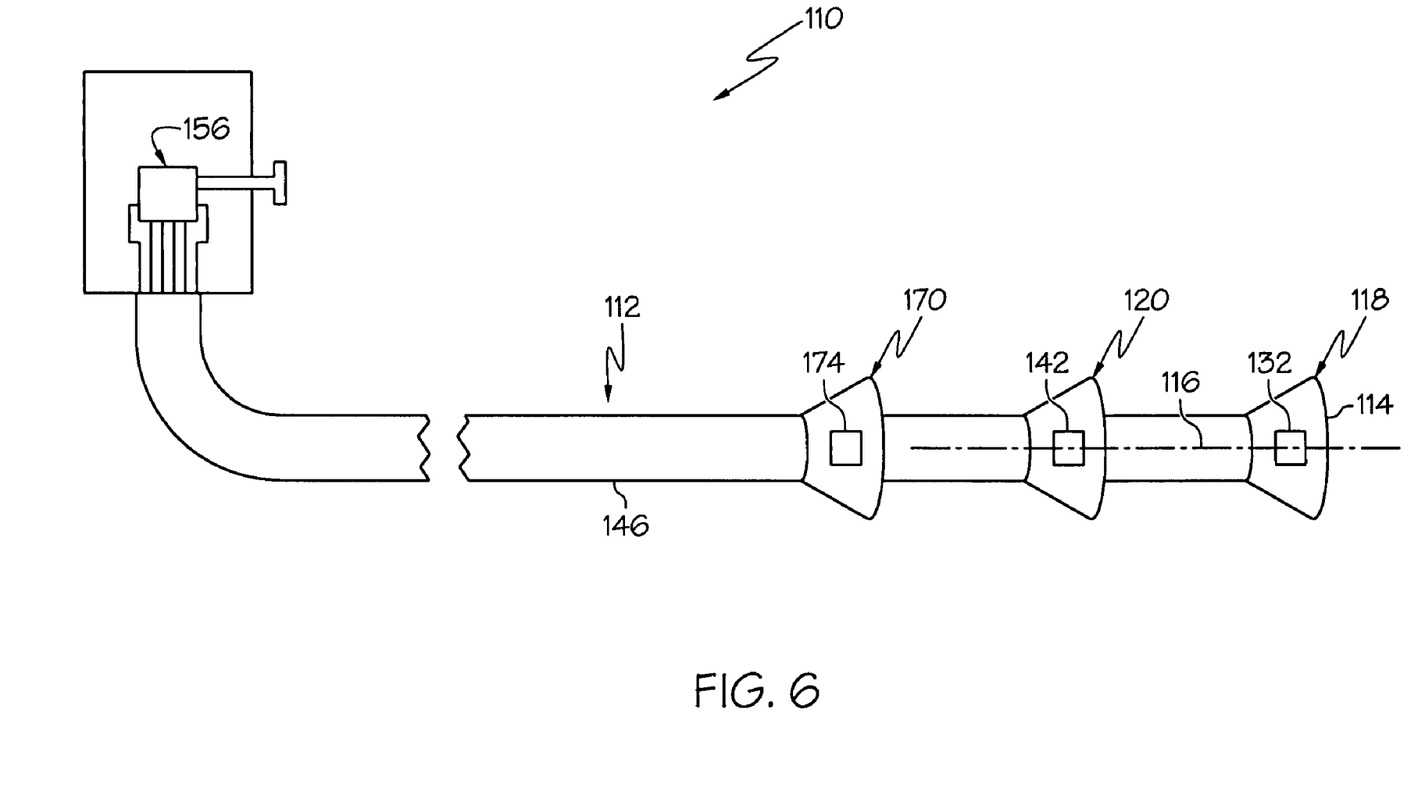
FIG. 6 is a view, as in FIG. 1, but showing a first alternate embodiment of the medical catheter, wherein the medical catheter is a sheath and is adapted for installation over a flexible endoscope insertion tube.
Figures 7, 8:
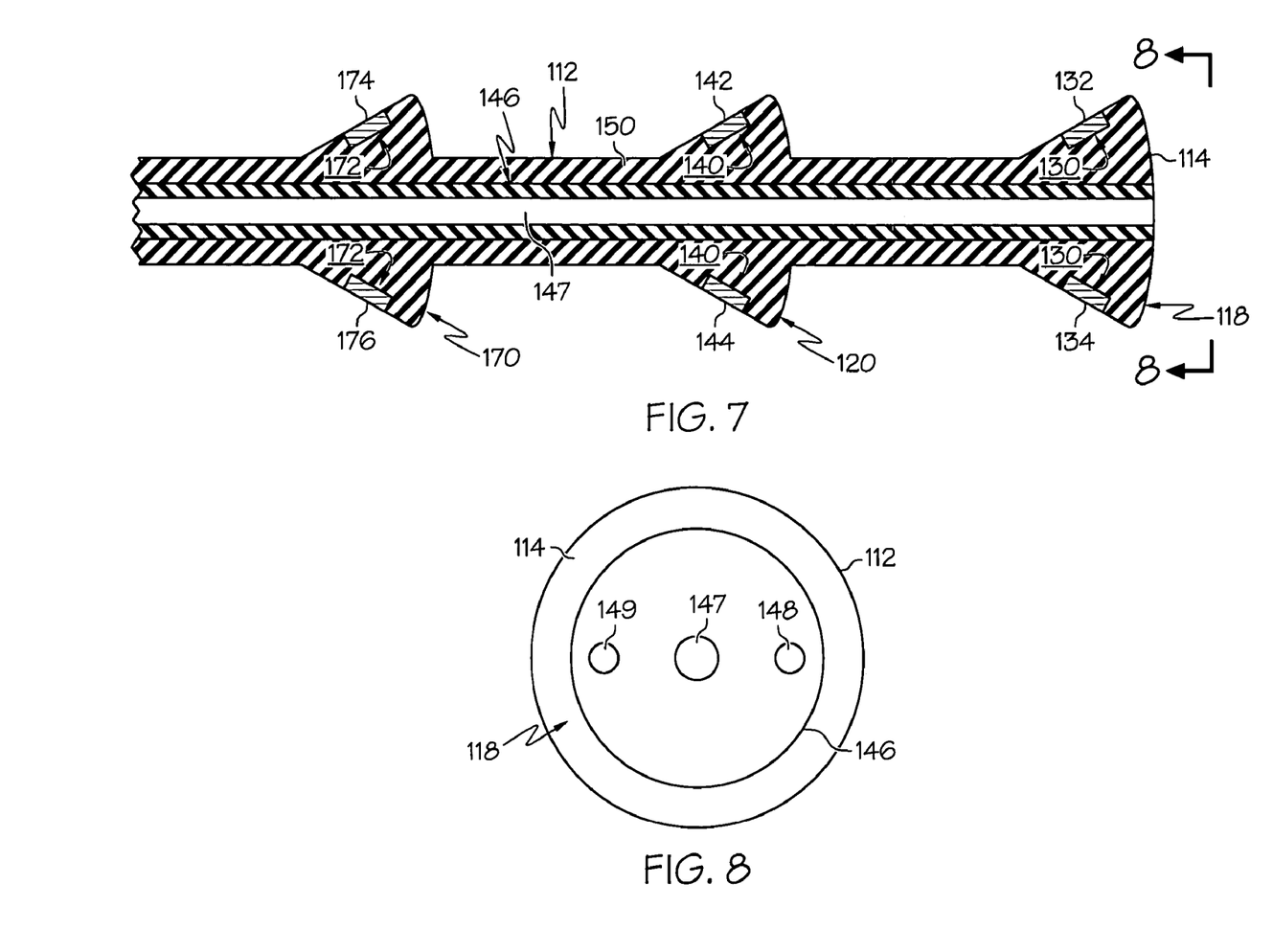
FIG. 7 is a cross sectional view of the distal portion of the medical catheter of FIG. 6, wherein the medical catheter of FIG. 7 has been rotated ninety degrees from the orientation shown in FIG. 6.
FIG. 8 is a view of the medical catheter of FIG. 7 taken along lines 8-8 of FIG. 7.

In a second implementation, shown in the first alternate embodiment of FIGS. 6-8, the medical catheter 112 is a sheath 150 and is adapted for installation over a flexible endoscope insertion tube 146 having a working channel 147. In one variation, the endoscope insertion tube 146 includes a visualization device 148 disposed at the distal end 114. In one modification, the endoscope insertion tube 146 includes an illumination device 149 disposed at the distal end 14.

In a first enablement of the first expression of the embodiment of FIGS. 1-5, the first and second exterior surfaces 26 and 36 have a substantially fixed shape when disposed within the body lumen 22. Thus, in this enablement, the first and second exterior surfaces 26 and 36 are substantially non-deformable when present in and moved through the body lumen 22.

Figure 9:
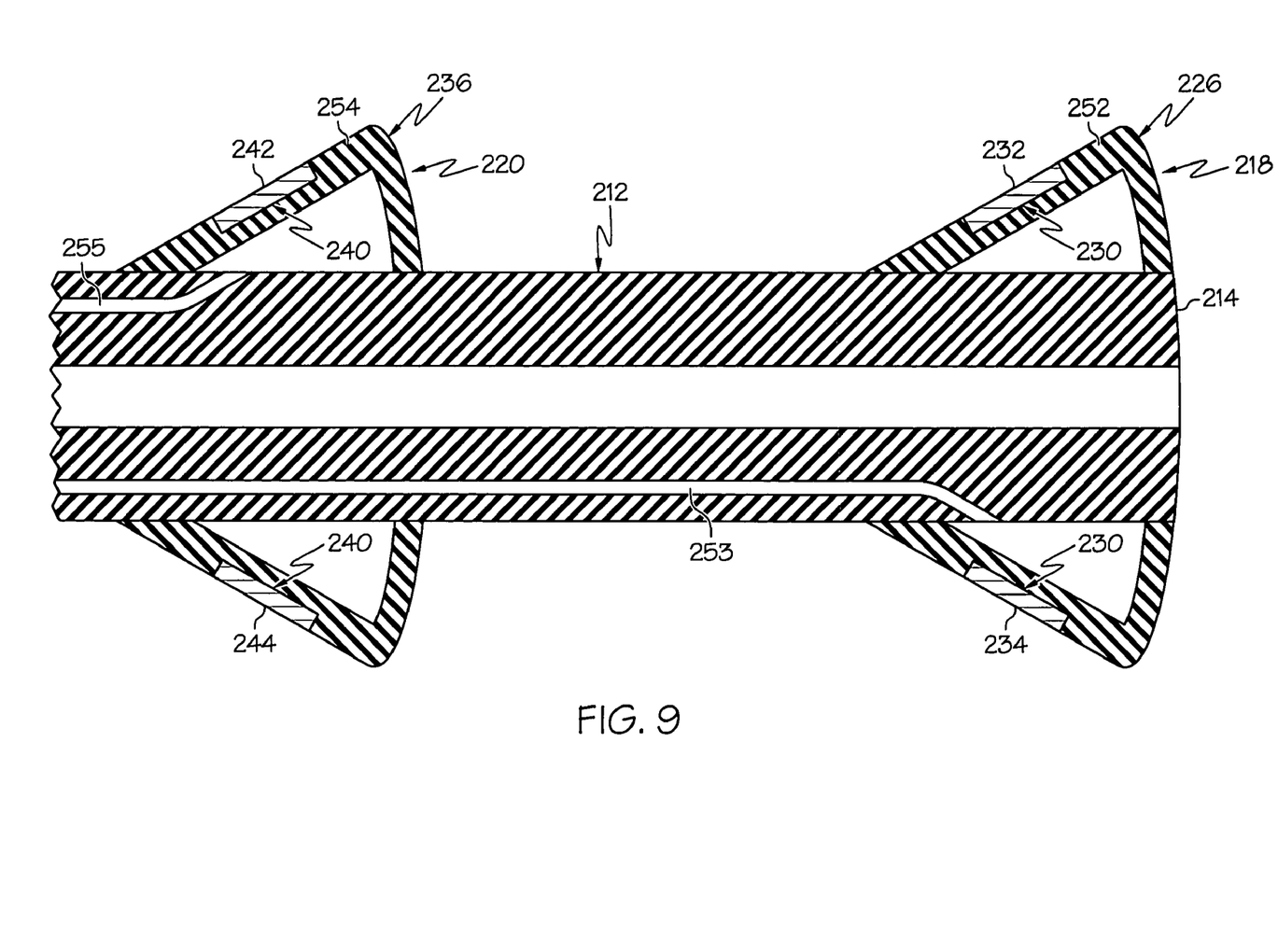
FIG. 9 is an enlarged cross-sectional view of a second alternate embodiment of the medical catheter showing two pods of the medical catheter, wherein each pod includes an inflatable balloon.

In a second enablement, shown in the second alternate embodiment of FIG. 9, the first pod 218 includes an inflatable first balloon 252, wherein the first exterior surface 226 is an inflated exterior surface of the first balloon 252, and the second pod 220 includes an inflatable second balloon 254, wherein the second exterior surface 236 is an inflated exterior surface of the second balloon 254. In one construction, the medical catheter 212 includes a first inflation lumen 253 in fluid communication with the first balloon 252 and a second inflation lumen 255 in fluid communication with the second balloon 254.

Figure 5:
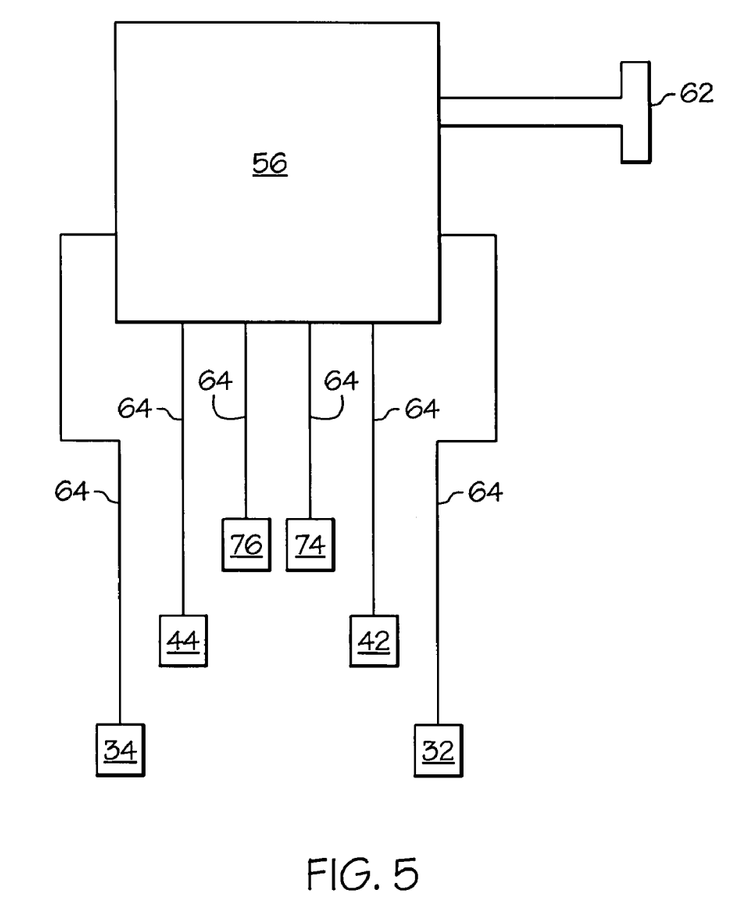
FIG. 5 is a schematic drawing showing the electrical connections between the controller of FIG. 1 and the electrodes of the pods of the medical catheter of FIG. 2.

In one extension of the first expression of the embodiment of FIGS. 1-5, the medical instrument 10 also includes a controller 56 adapted to energize the first electrode pair 30 for contraction of muscular lumen tissue 24 contacting the first electrode pair 30 and adapted to energize the second electrode pair 40 for contraction of muscular lumen tissue 24 contacting the second electrode pair 40. In one example, the medical instrument 10 includes a handpiece 58 attached to the proximal end 60 of the medical catheter 12, wherein the handpiece 58 includes the controller 56 having a button 62 for a user to activate the controller 56. In one variation, as shown in FIG. 5, wires 64 connect the controller 56 to the electrodes 32, 34, 42, and 44. In one illustration, the controller 56 uses the wires 64 to apply a positive DC voltage to electrodes 32 and 42 and a negative DC voltage to electrodes 34 and 44 at a predetermined frequency such as, for example, 50 Hertz.

In a first application, the controller 56 is adapted to substantially simultaneously energize the first and second electrode pairs 30 and 40 as long as the controller 56 is activated by a user. In this application, the speed of travel of the medical catheter 12 in the body lumen 22 from the simultaneous energizing is a predetermined speed, and the time for contracted muscular lumen tissue 24 no longer in contact with an energized electrode 32, 34, 42 and 44 to relax is a predetermined time (such as a speed and time determined by experimentation). In this application, the first and second electrode pairs 30 and 40 are longitudinally adjacent electrode pairs (meaning there are no longitudinally-intervening electrode pairs). In this application, the first and second electrode pairs 30 and 40 are longitudinally spaced apart a distance. The distance is chosen for contracted muscular lumen tissue 24 at a longitudinal location of the body lumen 22 contacted by the first electrode pair 30 to at least relax after the first electrode pair 30 moves past the longitudinal location and before the advancing second electrode pair 40 reaches the longitudinal location. In one illustration the contracted muscular lumen tissue 24 will at least reach a relaxed state if such distance is at least five centimeters. In one example, the controller 56 substantially simultaneously energizes the first and second electrode pairs 30 and 40 for a continuous period of time (such as until the distal end 14 of the medical catheter 12 is at its final location in the body lumen 22) at a predetermined frequency (such as, for example, 50 Hertz).

In a second application, the controller 56 is adapted to sequentially energize the first and second electrode pairs 30 and 40 as long as the controller 56 is activated by a user. In this application, the speed of travel of the medical catheter 12 in the body lumen 22 from the sequential energizing is a predetermined speed, and the time for contracted muscular lumen tissue 24 no longer in contact with an energized electrode 32, 34, 42 and 44 to relax is a predetermined time (such as a speed and time determined by experimentation). In this application the first and second electrode pairs 30 and 40 are longitudinally adjacent electrode pairs (meaning there are no longitudinally-intervening electrode pairs). In this application the first and second electrode pairs 30 and 40 are longitudinally spaced apart a distance. The distance is chosen for contracted muscular lumen tissue 24 at a longitudinal location of the body lumen 22 contacted by the first electrode pair 30 to at least relax after the first electrode pair 30 moves past the longitudinal location and before the advancing second electrode pair 40 reaches the longitudinal location. In one illustration, the contracted muscular lumen tissue 24 will at least reach a relaxed state if such distance is at least five centimeter. In one example, the controller 56 energizes the first electrode pair 30 for a period of time (such as five seconds) and then shuts off the first electrode pair 30 for a period of time (such as five seconds), then energizes the second electrode pair 40 for a period of time (such as five seconds) and then shuts off the second electrode pair 40 for a period of time (such as five seconds), then energizes the first electrode pair 30 for a period of time (such as five seconds) and then shuts off the first electrode pair 30 for a period of time (such as five seconds), then energizes the second electrode pair 40 for a period of time (such as five seconds) and then shuts off the second electrode pair 40 for a period of time (such as five seconds), etc., wherein during the time it takes for contracted muscular lumen tissue 24 no longer in contact with an energized electrode 32, 34, 42 and 44 to relax, the first electrode pair 30 leaves a lumen tissue location and the second electrode pair 40 contacts the same lumen tissue location.

It is noted that applicant was the first to realize that proper longitudinal spacing of the first and second pods 18 and 20 would make a multiple-pod medical catheter 12 workable as such proper spacing would prevent a second pod 20 from encountering muscular lumen tissue 24 that was still in a contracted state from a previously contacting first pod 18.

A first expression of the alternate embodiment of FIGS. 6-8 is for a medical instrument 110 including a medical catheter 112 and a controller 156. The medical catheter 112 is a sheath 150 and is adapted for installation over a flexible endoscope insertion tube 146. The installed medical catheter 112 has a distal end 114, a centerline 116, a circumferentially-protruding first pod 112 including electrodes 132 and 134, and a circumferentially-protruding second pod 120 including electrodes 142 and 144 as described for the medical catheter 12 in paragraph [0024]. The controller 156 is adapted to energize the first electrode pair 130 for contraction of muscular lumen tissue (shown as 24 in FIG. 2) contacting the first electrode pair 130 and is adapted to energize the second electrode pair 140 for contraction of muscular lumen tissue (shown as 24 in FIG. 2) contacting the second electrode pair 140.

It is noted that the second enablement, extensions, applications, etc. of the first expression of the embodiment of FIGS. 1-5 are equally applicable to the first expression of the alternate embodiment of FIGS. 6-8.

A method of the invention is for using a medical catheter 212, wherein the medical catheter 212 is as described for the medical catheter 10 in paragraph [0024] with the second enablement as described in paragraph [0028]. The method includes inserting the distal end 214 within the body lumen (shown as 22 in FIG. 2). The method includes manually advancing the medical catheter 212 within the body lumen a first distance with the first and second balloons 252 and 254 deflated and with the first and second electrode pairs 230 and 240 (of circumferentially-spaced-apart electrodes 232 & 234 and 242 & 244) not energized. The method includes inflating the first and second balloons 252 and 254. The method includes energizing the first electrode pair 230 after the first balloon 252 has been inflated. The method includes energizing the second electrode pair 240 after the second balloon 254 has been inflated.

In a first enablement of the method, the first and second electrode pairs 230 and 240 are substantially simultaneously energized for self-advancing the medical catheter 212 within the body lumen a second distance. In a second enablement, the first and second electrode pairs 230 and 240 are sequentially energized for self-advancing the medical catheter 212 within the body lumen a second distance. In a third enablement, the first and second electrode pairs 230 and 240 are substantially simultaneously energized during a certain time period(s) and are sequentially energized during a different time period(s).

In a first employment of the method, the medical catheter 212 is manually advanced before the first and second electrode pairs 230 and 240 are energized. In a second employment, the first and second electrode pairs 230 and 240 are energized before the medical catheter 212 is manually advanced.

In one utilization of the method, the body lumen is a colon of a human or other mammal. In another utilization, the body lumen is an upper gastrointestinal tract. In a further utilization, the body lumen is an artery lumen. Other body lumens are left to those skilled in the art.

In one embellishment of any of the embodiments and method, and with reference to FIGS. 1-2 and 6-7, the medical instrument 10 and 110 includes a circumferentially-protruding third pod 70 and 170 proximally longitudinally spaced apart from the second pod 20 and 120 and having an energizable third electrode pair 72 and 172 of circumferentially-spaced-apart electrodes 74 & 174 and 76 & 176. In one variation, as shown in FIG. 5, wires 64 electrically connect the controller 56 to the electrodes 32 and 34 of the first electrode pair 30, the electrodes 42 and 44 of the second electrode pair 40, and the electrodes 74 and 76 of the third electrode pair 72.

Several benefits and advantages are obtained from one or more of the expressions of several embodiments and the method of the invention. In one example, the pods are disposed proximate the distal end so that the self-advancing medical catheter will not form undesirable loops, as can be appreciated by those skilled in the art. In the same or a different example, each pod includes an inflatable balloon which supports the electrodes, which is deflated (resulting in a smaller catheter transverse cross-sectional size within the body lumen) when manual advancement of the medical catheter within the body lumen is desired, and which is inflated only when self-advancement of the medical catheter within the body lumen is desired. In the same or a different example, a controller simultaneously or sequentially energizes the first and second electrode pairs for more rapid advancement within the body lumen than is possible from a single electrode pair, wherein the electrode pairs are longitudinally spaced apart a distance ensuring that muscular lumen tissue contracted by one electrode pair will have enough time to relax before the self-advancing next electrode pair reaches the same muscular lumen tissue. In the same or a different example, the medical catheter is a sheath installed over an existing endoscope insertion tube improving the performance of existing endoscopes.

While the present invention has been illustrated by a description of several expressions of embodiments and a method, it is not the intention of the applicants to restrict or limit the spirit and scope of the appended claims to such detail. Numerous other variations, changes, and substitutions will occur to those skilled in the art without departing from the scope of the invention. For instance, the medical instrument of the invention has application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. A medical instrument comprising a medical catheter, wherein the medical catheter includes:
   a) a proximal end and a distal end, the distal end being insertable within a body lumen of a patient having muscular lumen tissue surrounding the body lumen;
   b) a centerline which defines a longitudinal axis when the medical catheter is in an unflexed state;
   c) a circumferentially-protruding first pod having a first exterior surface with a first proximally-tapering surface portion which includes an energizable first electrode pair of circumferentially-spaced-apart electrodes and which has a shape adapted to advance the first pod within the body lumen upon contraction of muscular lumen tissue contacting an energized first electrode pair; and
   d) a circumferentially-protruding second pod having a second exterior surface with a second proximally-tapering surface portion which includes an energizable second pair of circumferentially-spaced-apart electrodes and which has a shape adapted to advance the second pod within the body lumen upon contraction of muscular lumen tissue contacting an energized second electrode pair, wherein the second pod is proximally longitudinally spaced apart from the first pod.

2. The medical instrument of claim 1, wherein the medical catheter is a flexible endoscope insertion tube.

3. The medical instrument of claim 2, wherein the endoscope insertion tube includes a visualization device disposed at the distal end.

4. The medical instrument of claim 1, wherein the medical catheter is a sheath and is adapted for installation over a flexible endoscope insertion tube.

5. The medical instrument of claim 4, wherein the endoscope insertion tube includes a visualization device disposed at the distal end.

6. The medical instrument of claim 1, wherein the first and second exterior surfaces have a substantially fixed shape when disposed within the body lumen.

7. The medical instrument of claim 1, wherein the first pod includes an inflatable first balloon, wherein the first exterior surface is an inflated exterior surface of the first balloon, wherein the second pod includes an inflatable second balloon, wherein the second exterior surface is an inflated exterior surface of the second balloon.

8. The medical instrument of claim 1, also including a controller adapted to energize the first electrode pair for contraction of muscular lumen tissue contacting the first electrode pair and adapted to energize the second electrode pair for contraction of muscular lumen tissue contacting the second electrode pair.

9. The medical instrument of claim 8, wherein the controller is adapted to substantially simultaneously energize the first and second electrode pairs as long as the controller is activated by a user, wherein the speed of travel of the medical catheter in the body lumen from the simultaneous energizing is a predetermined speed, wherein the time for contracted muscular lumen tissue no longer in contact with an energized electrode to relax is a predetermined time, wherein the first and second electrode pairs are longitudinally adjacent electrode pairs and are longitudinally spaced apart a distance, and wherein the distance is chosen for contracted muscular lumen tissue at a longitudinal location of the body lumen contacted by the first electrode pair to at least relax after the first electrode pair moves past the longitudinal location and before the advancing second electrode pair reaches the longitudinal location.

10. The medical instrument of claim 8, wherein the controller is adapted to sequentially energize the first and second electrode pairs as long as the controller is activated by a user, wherein the speed of travel of the medical catheter in the body lumen from the sequential energizing is a predetermined speed, wherein the time for contracted muscular lumen tissue no longer in contact with an energized electrode to relax is a predetermined time, wherein the first and second electrode pairs are longitudinally adjacent electrode pairs and are longitudinally spaced apart a distance, and wherein the distance is chosen for contracted muscular lumen tissue at a longitudinal location of the body lumen contacted by the first electrode pair to at least relax after the first electrode pair moves past the longitudinal location and before the advancing second electrode pair reaches the longitudinal location.

11. A medical instrument comprising:
 a) a medical catheter, wherein the medical catheter is a sheath and is adapted for installation over a flexible endoscope insertion tube, and wherein the installed medical catheter includes:
  (1) a proximal end and a distal end, the distal end being insertable within a body lumen of a patient having muscular lumen tissue surrounding the body lumen;
  (2) a centerline which defines a longitudinal axis when the installed medical catheter is in an unflexed state;
  (3) a circumferentially-protruding first pod having a first exterior surface with a first proximally-tapering surface portion which includes an energizable first electrode pair of circumferentially-spaced-apart electrodes and which has a shape adapted to advance the first pod within the body lumen upon contraction of muscular lumen tissue contacting an energized first electrode pair; and
  (4) a circumferentially-protruding second pod having a second exterior surface with a second proximally-tapering surface portion which includes an energizable second pair of circumferentially-spaced-apart electrodes and which has a shape adapted to advance the second pod within the body lumen upon contraction of muscular lumen tissue contacting an energized second electrode pair, wherein the second pod is proximally longitudinally spaced apart from the first pod; and
 b) a controller adapted to energize the first electrode pair for contraction of muscular lumen tissue contacting the first electrode pair and adapted to energize the second electrode pair for contraction of muscular lumen tissue contacting the second electrode pair.

12. The medical instrument of claim 11, wherein the first and second exterior surfaces have a substantially fixed shape when disposed within the body lumen.

13. The medical instrument of claim 11, wherein the first pod includes an inflatable first balloon, wherein the first exterior surface is an inflated exterior surface of the first balloon, wherein the second pod includes an inflatable second balloon, wherein the second exterior surface is an inflated exterior surface of the second balloon.

14. The medical instrument of claim 11, wherein the controller is adapted to substantially simultaneously energize the first and second electrode pairs as long as the controller is activated by a user, wherein the speed of travel of the medical catheter in the body lumen from the simultaneous energizing is a predetermined speed, wherein the time for contracted muscular lumen tissue no longer in contact with an energized electrode to relax is a predetermined time, wherein the first and second electrode pairs are longitudinally adjacent electrode pairs and are longitudinally spaced apart a distance, and wherein the distance is chosen for contracted muscular lumen tissue at a longitudinal location of the body lumen contacted by the first electrode pair to at least relax after the first electrode pair moves past the longitudinal location and before the advancing second electrode pair reaches the longitudinal location.

15. The medical instrument of claim 11, wherein the controller is adapted to sequentially energize the first and second electrode pairs as long as the controller is activated by a user, wherein the speed of travel of the medical catheter in the body lumen from the sequential energizing is a predetermined speed, wherein the time for contracted muscular lumen tissue no longer contacted by an energized electrode to relax is a predetermined time, wherein the first and second electrode pairs are longitudinally adjacent electrode pairs and are longitudinally spaced apart a distance, and wherein the distance is chosen for contracted muscular lumen tissue at a longitudinal location of the body lumen contacted by the first electrode pair to at least relax after the first electrode pair moves past the longitudinal location and before the advancing second electrode pair reaches the longitudinal location.

16. A method for using a medical catheter, wherein the medical catheter includes: a proximal end and a distal end, the distal end being insertable within a body lumen of a patient having muscular lumen tissue surrounding the body lumen; a centerline which defines a longitudinal axis when the medical catheter is in an unflexed state; a circumferentially-protruding first pod having a first exterior surface with a first proximally-tapering surface portion which includes an energizable first electrode pair of circumferentially-spaced-apart electrodes and which has a shape adapted to advance the first pod within the body lumen upon contraction of muscular lumen tissue contacting an energized first electrode pair, wherein the first pod includes an inflatable first balloon, and wherein the first exterior surface is an inflated exterior surface of the first balloon; and a circumferentially-protruding second pod having a second exterior surface with a second proximally-tapering surface portion which includes an energizable second pair of circumferentially-spaced-apart electrodes and which has a shape adapted to advance the second pod within the body lumen upon contraction of muscular lumen tissue contacting an energized second electrode pair, wherein the second pod is proximally longitudinally spaced apart from the first pod, wherein the second pod includes an inflatable second balloon, and wherein the second exterior surface is an inflated exterior surface of the second balloon, and wherein the method includes:
 a) inserting the distal end within the body lumen;
 b) manually advancing the medical catheter within the body lumen a first distance with the first and second balloons deflated and with the first and second electrode pairs not energized;
 c) inflating the first and second balloons;
 d) energizing the first electrode pair after the first balloon has been inflated; and
 e) energizing the second electrode pair after the second balloon has been inflated.

17. The method of claim 16, wherein the first and second electrode pairs are substantially simultaneously energized for self-advancing the medical catheter within the body lumen a second distance.

18. The method of claim 16, wherein the first and second electrode pairs are sequentially energized for self-advancing the medical catheter within the body lumen a second distance.

19. The method of claim 16, wherein the medical catheter is manually advanced before the first and second electrode pairs are energized.

20. The method of claim 16, wherein the first and second electrode pairs are energized before the medical catheter is manually advanced.

* * * * *